United States Patent
Jou et al.

(10) Patent No.: US 12,227,546 B2
(45) Date of Patent: Feb. 18, 2025

(54) PLASMID ENCODING A C-TERMINAL FRAGMENT OF PARASPECKLE COMPONENT 1 FOR TREATING TUMORS

(71) Applicant: Academia Sinica, Taipei (TW)

(72) Inventors: Yuh-Shan Jou, Taipei (TW);
Yaw-Dong Lang, Taipei (TW);
Hsi-Wen Yeh, Tainan (TW)

(73) Assignee: ACADEMIA SINICA, Taipei (TW)

( * ) Notice: Subject to any disclaimer, the term of this patent is extended or adjusted under 35 U.S.C. 154(b) by 1221 days.

(21) Appl. No.: 16/970,350

(22) PCT Filed: Feb. 12, 2019

(86) PCT No.: PCT/US2019/017591
§ 371 (c)(1),
(2) Date: Aug. 15, 2020

(87) PCT Pub. No.: WO2019/160840
PCT Pub. Date: Aug. 22, 2019

(65) Prior Publication Data
US 2021/0087239 A1   Mar. 25, 2021

Related U.S. Application Data

(60) Provisional application No. 62/631,503, filed on Feb. 16, 2018.

(51) Int. Cl.
| | |
|---|---|
| *C12N 15/00* | (2006.01) |
| *A61K 48/00* | (2006.01) |
| *C07K 14/47* | (2006.01) |
| *C12N 15/63* | (2006.01) |
| *A61K 38/00* | (2006.01) |

(52) U.S. Cl.
CPC ...... *C07K 14/4702* (2013.01); *A61K 48/0041* (2013.01); *A61K 48/005* (2013.01); *C12N 15/63* (2013.01); *A61K 38/00* (2013.01)

(58) Field of Classification Search
None
See application file for complete search history.

(56) References Cited

U.S. PATENT DOCUMENTS

2016/0137725 A1 * 5/2016 Gu ..................... C07K 16/18
530/387.3

OTHER PUBLICATIONS

Guallar (Nature Genetics, Mar. 2018, vol. 50, p. 443-451).*
Fox (Current Biol., 2002, vol. 12, No. 1, p. 13-25.*
Yeh (Nature Cell Biol, 2018, vol. 20, p. 479-491).*
Wang (Oncoimmunology, 2018, vol. 7, No. 11, e1503913).*
International Search Report for PCT/US2019/017591, dated Apr. 24, 2019.
Written Opinion of International Search Authority for PCT/US2019/017591, dated Apr. 24, 2019.

* cited by examiner

*Primary Examiner* — Michael C Wilson
(74) *Attorney, Agent, or Firm* — Hsiu-Ming Saunders; INTELLECTUAL PROPERTY CONNECTIONS, INC.

(57) ABSTRACT

An isolated nucleic acid encoding a C-terminal fragment of paraspeckle component 1 (PSPC1) is disclosed. The C-terminal fragment of the PSPC1 comprises an extension of more than 10 but no greater than 131 amino acid residues with its C-terminal amino acid identical to the C-terminus of the PSPC1 sequence SEQ ID NO: 3 and exhibits a biological activity against tumor cells. The tumor cells are associated with either PSPC1 or protein tyrosine kinase 6 (PTK6), or both. The anti-tumor activity is at least one selected from the group consisting of: (a) suppressing tumor cell growth; (b) suppressing tumor cell progression; (c) suppressing tumor cell metastasis; (d) decreasing PSPC1 expression; and (e) decreasing oncogenic PTK6 expression in cytoplasm. Also disclosed is a peptide comprising a C-terminal fragment sequence of PSPC1. A reagent kit and method for predicting tumor progression, metastasis, and prognosis in a cancer patient are also disclosed.

7 Claims, 8 Drawing Sheets
Specification includes a Sequence Listing.

SEQUENCE LISTING

<160> NUMBER OF SEQ ID NOS: 8

<210> SEQ ID NO 1

<211> LENGTH: 131
<212> TYPE: PRT
<213> ORGANISM: Homo sapiens

<400> SEQUENCE: 1

Met Gly Asp Met Gly Pro Arg Gly Ala Ile Asn Met Gly Asp Ala Phe
1               5                   10                  15

Ser Pro Ala Pro Ala Gly Asn Gln Gly Pro Pro Met Met Gly Met
            20                  25                  30

Asn Met Asn Asn Arg Ala Thr Ile Pro Gly Pro Pro Met Gly Pro Gly
        35                  40                  45

Pro Ala Met Gly Pro Glu Gly Ala Ala Asn Met Gly Thr Pro Met Met
    50                  55                  60

Pro Asp Asn Gly Ala Val His Asn Asp Arg Phe Pro Gln Gly Pro Pro
65                  70                  75                  80

Ser Gln Met Gly Ser Pro Met Gly Ser Arg Thr Gly Ser Glu Thr Pro
                85                  90                  95

Gln Ala Pro Met Ser Gly Val Gly Pro Val Ser Gly Pro Gly Gly
            100                 105                 110

Phe Gly Arg Gly Ser Gln Gly Gly Asn Phe Glu Gly Pro Asn Lys Arg
        115                 120                 125

Arg Arg Tyr
    130

<210> SEQ ID NO 2
<211> LENGTH: 2401
<212> TYPE: DNA
<213> ORGANISM: Homo sapiens

<400> SEQUENCE: 2
gagtgcgcag gcgcgtcgtt ccggcgccgg ctttggcgga ggggtgggac ttgcaccggc      60
gtctcttctt ctaactgcag tttgtggcag cgccattttg aatgtgcagc tgcagcgggc     120
gcctgtatcc ggtgtccgag gcgaactcag taagatgatg ttaagaggaa acctgaagca     180
agtgcgcatt gagaaaaacc cggcccgcct tcgcgccctg agtccgcgg tgggcgagag      240 cgagccggcg gccgcggcag ccatggcgct cgctcttgcc ggggagccgg caccgcccgc     300
gcccgcgcct ccagaggacc acccggacga ggagatgggg ttcactatcg acatcaagag     360
tttcctcaag ccgggcgaga agacgtacac gcagcgctgc cgcctcttcg tgggaaatct     420
gcccaccgac atcacggagg aggacttcaa gaggctcttc gaacgctatg gcgagcccag     480
cgaagtcttc atcaaccggg accgtggctt cggcttcatc cgcttggaat ccagaacccc     540
tgctgaaatt gcaaaagcag agctggacgg caccattctc aagagcagac ctctacggat     600
tcgcttcgct acacatggag cagccttgac tgtcaagaac cttctccag ttgtttccaa      660 tgagctgcta gagcaagcat ttctcagtt tggtccagta gagaaagctg ttgtggttgt      720
ggatgatcgc ggtagagcta caggaaaagg ttttgtagag tttgcagcaa aacctcctgc     780
acgaaaggct ctggaaagat gtggtgatgg ggcattcttg ctaacaacga cccctcgtcc     840
agtcattgtg gaacccatgg agcagtttga tgatgaagat ggcttgccag agaagctgat     900
gcagaaaact caacaatatc ataaggaaag agaacaacca ccacgttttg ctcaacctgg     960
gacatttgaa tttgagtatg catctcgatg gaaggctctt gatgaaatgg aaaagcagca    1020
gcgtgagcag gttgatagaa acatcagaga agccaaagag aaactggagg cagaaatgga    1080
agcagctagg catgaacacc aattaatgct aatgaggcaa gatctaatga ggcgtcaaga    1140

-continued

```
agaactcaga cgcttggaag aactcagaaa ccaagagttg caaaaacgga agcaaataca    1200
actaagacat gaagaggagc atcggcggcg tgaggaagaa atgatccgac acagagaaca    1260
ggaggaactg aggcgacagc aagagggctt aagccaaac tacatggaaa atagagaaca    1320
ggaaatgaga atgggtgata tgggtccccg tggagcaata acatgggag atgcgtttag    1380 cccagcccct gctggtaacc aaggtcctcc tccaatgatg ggtatgaata tgaacaacag    1440
agcaactata cctggcccac caatgggtcc tggtcctgcc atgggaccag aaggagccgc    1500
aaatatggga actccaatga tgccagataa tggagcagtg cacaatgaca gatttcctca    1560
aggaccacca tctcagatgg gttcacctat ggggagtaga acaggttctg aaacccctca    1620
agcaccaatg agtggtgtag gtcctgtgag tggtggtcct ggtggctttg gtagaggaag    1680 tcaaggggc aactttgaag gccctaataa gcgtcgtaga tattaaacat tcgttcattc    1740
ctggctatct agaaaaaaaa aagtcagtgg tatgccttta tacttttacc tgttatctgg    1800
aagaaatggt tttattgtta atgtatgtag acttaaaagt ttttttttt ttgtaaaact    1860 tgaggttttt gtattttct ttattcatga gctttgtaga ttagaatggt aatgatgctc    1920
atcattttga atgttgaaat gtgtttgtga ctttagctaa atataagtat tccatagtac    1980
tgtgaaatct atgtagttaa tctcaataaa gaaatcattt tggataattt aaaactgtta    2040
ttagtggtat tctcttacgg tcttactaaa cttgctgta acagtaatgc tttggttgct    2100
ttaactaatc ctatcattaa aaatgaaaat gattttgctt tttaatttgc gcaagtagca    2160
ctaaagatag aagcttaatt aatgaaagct aatgtcaata aggggtagat agagtagtat    2220
atgtgggggt gggagggtat gggagtttaa tttgtataaa ccactgatgt tctgtgaaat    2280
cggaatttcc agctacattt catatagctt ctgaatattc aggtattctg agacagatta    2340
ttaaggatat ctttgtcctg tgctgatttt tccaaataaa tcttttcat cttgaaaaaa    2400 a                                                                    2401
```

<210> SEQ ID NO 3
<211> LENGTH: 523
<212> TYPE: PRT
<213> ORGANISM: Homo sapiens

<400> SEQUENCE: 3

```
Met Met Leu Arg Gly Asn Leu Lys Gln Val Arg Ile Glu Lys Asn Pro
1               5                   10                  15

Ala Arg Leu Arg Ala Leu Glu Ser Ala Val Gly Glu Ser Glu Pro Ala
            20                  25                  30

Ala Ala Ala Ala Met Ala Leu Ala Leu Ala Gly Glu Pro Ala Pro Pro
        35                  40                  45

Ala Pro Ala Pro Pro Glu Asp His Pro Asp Glu Met Gly Phe Thr
    50                  55                  60

Ile Asp Ile Lys Ser Phe Leu Lys Pro Gly Glu Lys Thr Tyr Thr Gln
65                  70                  75                  80

Arg Cys Arg Leu Phe Val Gly Asn Leu Pro Thr Asp Ile Thr Glu Glu
                85                  90                  95

Asp Phe Lys Arg Leu Phe Glu Arg Tyr Gly Glu Pro Ser Glu Val Phe
            100                 105                 110

Ile Asn Arg Asp Arg Gly Phe Gly Phe Ile Arg Leu Glu Ser Arg Thr
        115                 120                 125

Leu Ala Glu Ile Ala Lys Ala Glu Leu Asp Gly Thr Ile Leu Lys Ser
    130                 135                 140
```

Arg Pro Leu Arg Ile Arg Phe Ala Thr His Gly Ala Ala Leu Thr Val
145                 150                 155                 160

Lys Asn Leu Ser Pro Val Val Ser Asn Glu Leu Leu Glu Gln Ala Phe
            165                 170                 175

Ser Gln Phe Gly Pro Val Glu Lys Ala Val Val Val Asp Asp Arg
        180                 185                 190

Gly Arg Ala Thr Gly Lys Gly Phe Val Glu Phe Ala Ala Lys Pro Pro
    195                 200                 205

Ala Arg Lys Ala Leu Glu Arg Cys Gly Asp Gly Ala Phe Leu Leu Thr
    210                 215                 220

Thr Thr Pro Arg Pro Val Ile Val Glu Pro Met Glu Gln Phe Asp Asp
225                 230                 235                 240

Glu Asp Gly Leu Pro Glu Lys Leu Met Gln Lys Thr Gln Gln Tyr His
            245                 250                 255

Lys Glu Arg Glu Gln Pro Pro Arg Phe Ala Gln Pro Gly Thr Phe Glu
        260                 265                 270

Phe Glu Tyr Ala Ser Arg Trp Lys Ala Leu Asp Glu Met Glu Lys Gln
        275                 280                 285

Gln Arg Glu Gln Val Asp Arg Asn Ile Arg Glu Ala Lys Glu Lys Leu
    290                 295                 300

Glu Ala Glu Met Glu Ala Ala Arg His Glu His Gln Leu Met Leu Met
305                 310                 315                 320

Arg Gln Asp Leu Met Arg Arg Gln Glu Glu Leu Arg Arg Leu Glu Glu
            325                 330                 335

Leu Arg Asn Gln Glu Leu Gln Lys Arg Lys Gln Ile Gln Leu Arg His
        340                 345                 350

Glu Glu Glu His Arg Arg Arg Glu Glu Glu Met Ile Arg His Arg Glu
        355                 360                 365

Gln Glu Glu Leu Arg Arg Gln Gln Glu Gly Phe Lys Pro Asn Tyr Met
    370                 375                 380

Glu Asn Arg Glu Gln Glu Met Arg Met Gly Asp Met Gly Pro Arg Gly
385                 390                 395                 400

Ala Ile Asn Met Gly Asp Ala Phe Ser Pro Ala Pro Ala Gly Asn Gln
            405                 410                 415

Gly Pro Pro Pro Met Met Gly Met Asn Met Asn Asn Arg Ala Thr Ile
        420                 425                 430

Pro Gly Pro Pro Met Gly Pro Gly Pro Ala Met Gly Pro Glu Gly Ala
    435                 440                 445

Ala Asn Met Gly Thr Pro Met Met Pro Asp Asn Gly Ala Val His Asn
    450                 455                 460

Asp Arg Phe Pro Gln Gly Pro Ser Gln Met Gly Ser Pro Met Gly
465                 470                 475                 480

Ser Arg Thr Gly Ser Glu Thr Pro Gln Ala Pro Met Ser Gly Val Gly
            485                 490                 495

Pro Val Ser Gly Gly Pro Gly Phe Gly Arg Gly Ser Gln Gly Gly
        500                 505                 510

Asn Phe Glu Gly Pro Asn Lys Arg Arg Arg Tyr
        515                 520

<210> SEQ ID NO 4
<211> LENGTH: 451
<212> TYPE: PRT
<213> ORGANISM: Homo sapiens

<400> SEQUENCE: 4

```
Met Val Ser Arg Asp Gln Ala His Leu Gly Pro Lys Tyr Val Gly Leu
1               5                   10                  15

Trp Asp Phe Lys Ser Arg Thr Asp Glu Glu Leu Ser Phe Arg Ala Gly
            20                  25                  30

Asp Val Phe His Val Ala Arg Lys Glu Glu Gln Trp Trp Trp Ala Thr
        35                  40                  45

Leu Leu Asp Glu Ala Gly Gly Ala Val Ala Gln Gly Tyr Val Pro His
    50                  55                  60

Asn Tyr Leu Ala Glu Arg Glu Thr Val Glu Ser Glu Pro Trp Phe Phe
65                  70                  75                  80

Gly Cys Ile Ser Arg Ser Glu Ala Val Arg Arg Leu Gln Ala Glu Gly
                85                  90                  95

Asn Ala Thr Gly Ala Phe Leu Ile Arg Val Ser Glu Lys Pro Ser Ala
                100                 105                 110

Asp Tyr Val Leu Ser Val Arg Asp Thr Gln Ala Val Arg His Tyr Lys
            115                 120                 125

Ile Trp Arg Arg Ala Gly Gly Arg Leu His Leu Asn Glu Ala Val Ser
        130                 135                 140

Phe Leu Ser Leu Pro Glu Leu Val Asn Tyr His Arg Ala Gln Ser Leu
145                 150                 155                 160

Ser His Gly Leu Arg Leu Ala Ala Pro Cys Arg Lys His Glu Pro Glu
                165                 170                 175

Pro Leu Pro His Trp Asp Asp Trp Glu Arg Pro Arg Glu Glu Phe Thr
                180                 185                 190

Leu Cys Arg Lys Leu Gly Ser Gly Tyr Phe Gly Glu Val Phe Glu Gly
            195                 200                 205

Leu Trp Lys Asp Arg Val Gln Val Ala Ile Lys Val Ile Ser Arg Asp
    210                 215                 220

Asn Leu Leu His Gln Gln Met Leu Gln Ser Glu Ile Gln Ala Met Lys
225                 230                 235                 240

Lys Leu Arg His Lys His Ile Leu Ala Leu Tyr Ala Val Val Ser Val
                245                 250                 255

Gly Asp Pro Val Tyr Ile Ile Thr Glu Leu Met Ala Lys Gly Ser Leu
                260                 265                 270

Leu Glu Leu Leu Arg Asp Ser Asp Glu Lys Val Leu Pro Val Ser Glu
            275                 280                 285

Leu Leu Asp Ile Ala Trp Gln Val Ala Glu Gly Met Cys Tyr Leu Glu
    290                 295                 300

Ser Gln Asn Tyr Ile His Arg Asp Leu Ala Ala Arg Asn Ile Leu Val
305                 310                 315                 320

Gly Glu Asn Thr Leu Cys Lys Val Gly Asp Phe Gly Leu Ala Arg Leu
                325                 330                 335

Ile Lys Glu Asp Val Tyr Leu Ser His Asp His Asn Ile Pro Tyr Lys
                340                 345                 350

Trp Thr Ala Pro Glu Ala Leu Ser Arg Gly His Tyr Ser Thr Lys Ser
            355                 360                 365

Asp Val Trp Ser Phe Gly Ile Leu Leu His Glu Met Phe Ser Arg Gly
    370                 375                 380

Gln Val Pro Tyr Pro Gly Met Ser Asn His Glu Ala Phe Leu Arg Val
385                 390                 395                 400

Asp Ala Gly Tyr Arg Met Pro Cys Pro Leu Glu Cys Pro Pro Ser Val
                405                 410                 415
```

```
His Lys Leu Met Leu Thr Cys Trp Cys Arg Asp Pro Glu Gln Arg Pro
            420                 425                 430

Cys Phe Lys Ala Leu Arg Glu Arg Leu Ser Ser Phe Thr Ser Tyr Glu
        435                 440                 445

Asn Pro Thr
    450

<210> SEQ ID NO 5
<211> LENGTH: 14
<212> TYPE: PRT
<213> ORGANISM: Artificial Sequence
<220> FEATURE:
<223> OTHER INFORMATION: phosphopeptide amino acid sequence with Y
      phosphorylated

<400> SEQUENCE: 5

Cys Gly Gly Asn Phe Glu Gly Pro Asn Lys Arg Arg Arg Tyr
1               5                   10

<210> SEQ ID NO 6
<211> LENGTH: 42
<212> TYPE: DNA
<213> ORGANISM: Artificial Sequence
<220> FEATURE:
<223> OTHER INFORMATION: Y523F-F

<400> SEQUENCE: 6
ccctaataag cgtcgtagat tttaatctag agggccctat tc                      42

<210> SEQ ID NO 7
<211> LENGTH: 41
<212> TYPE: DNA
<213> ORGANISM: Artificial Sequence
<220> FEATURE:
<223> OTHER INFORMATION: Y523F-R

<400> SEQUENCE: 7
gaataggccc tctagattaa aatctacgac gcttattagg g                       41

<210> SEQ ID NO 8
<211> LENGTH: 13
<212> TYPE: PRT
<213> ORGANISM: Artificial Sequence
<220> FEATURE:
<223> OTHER INFORMATION: C-terminal 511-523 of PSPC1

<400> SEQUENCE: 8

Gly Gly Asn Phe Glu Gly Pro Asn Lys Arg Arg Arg Tyr
1               5                   10
```

PLASMID ENCODING A C-TERMINAL FRAGMENT OF PARASPECKLE COMPONENT 1 FOR TREATING TUMORS

REFERENCE TO RELATED APPLICATION

This application is a national stage application (under 35 U.S.C. 371) of PCT/US2019/017591 filed on 12 Feb. 2019, which claims priority to U.S. provisional application 62/631,503 filed on 16 Feb. 2018, all of which are herein incorporated by reference in their entireties.

FIELD OF THE INVENTION

The present invention relates generally to Paraspeckle component 1 (PSPC1).

BACKGROUND OF THE INVENTION

Protein tyrosine kinase 6 (PTK6) has been reported as an interacting partner of PSPC1. The function of PTK6 seems to depend on cellular context of cell types, differentiation states and its subcellular localizations. Nuclear PTK6 phosphorylates some RNA-binding proteins such as Sam68 and PSF to play as tumor suppressive role to modulate cell growth. Conversely, cytoplasmic PTK6 phosphorylates more than 30 intracellular targets for promoting oncogenic function. However, there is a need for understanding the detail mechanisms of PTK6 subcellular localizations.

SUMMARY OF THE INVENTION

In one aspect, the invention relates to an isolated nucleic acid encoding a C-terminal fragment of paraspeckle component 1 (PSPC1), wherein the C-terminal fragment of the PSPC1 comprises an extension of more than 10 but no greater than 131 amino acid residues with its C-terminal amino acid identical to the C-terminus of the PSPC1 sequence SEQ ID NO: 3 and exhibits a biological activity against tumor cells.

The C-terminal fragment of PSPC1 comprises an amino acid sequence C-terminal to the amino acid Arg at position 392 of SEQ ID NO: 3.

The isolated nucleic acid may be a DNA or an RNA molecule.

In another aspect, the invention relates to an isolated peptide with more than 10 but no greater than 131 amino acids residues in length, comprising an amino acid sequence that is at least 90% identical to a C-terminal fragment of paraspeckle component 1 (PSPC1), the C-terminal fragment of the PSPC1 comprising an extension of more than 10 but no greater than 131 amino acid residues with its C-terminal amino acid identical to the C-terminus of the PSPC1 sequence SEQ ID NO: 3, wherein the isolated peptide exhibits a biological activity against tumor cells.

In one embodiment, the tumor cells are associated with either PSPC1 or protein tyrosine kinase 6 (PTK6), or both.

In another embodiment, the tumor cells overexpress PSPC1 or PTK6, or both.

In another embodiment, the C-terminal fragment of the PSPC1 comprises the amino acid sequence of SEQ ID NO: 1.

In another embodiment, the isolated peptide comprises an amino acid sequence that is at least 95% identical to SEQ ID NO: 1.

In another embodiment, the isolated peptide comprises amino acid residues from Met 393 to Tyr 523 of SEQ ID NO: 3.

In another embodiment, the isolated nucleic acid or peptide of the invention exhibits anti-tumor biological activity that is at least one selected from the group consisting of: (a) suppressing tumor cell growth; (b) suppressing tumor cell progression; (c) suppressing tumor cell metastasis; (d) decreasing PSPC1 expression; and (e) decreasing oncogenic PTK6 expression in cytoplasm.

In another embodiment, the isolated nucleic acid or peptide of the invention is conjugated to, or forms a complex with, a component selected from the group consisting of polymers, polymeric micelles, lipoprotein-based drug carriers, nanoparticle drug carriers, micelles, liposomes, dendrimers, zwitterionic carbon dots, quantum dots, a lipid, a peptide, a polypeptide, and a protein.

Further in another aspect, the invention relates to a conjugate or a complex comprising: (i) an isolated nucleic acid or an isolated peptide of the invention; and (ii) a component, being selected from the group consisting of polymers, polymeric micelles, lipoprotein-based drug carriers, nanoparticle drug carriers, micelles, liposomes, dendrimers, zwitterionic carbon dots, quantum dots, a lipid, a peptide, a polypeptide, and a protein; wherein the isolated nucleic acid or peptide is conjugated to, or forms a complex with, the component.

The component may be polyethylenimine (PEI), polypropylenimine (PPI) or a cationic polymer.

The component may be a copolymer, which may further conjugate to a nuclear localization signal peptide.

The quantum dots may be densely decorated with a nuclear localization sequence signal.

The component exhibits a feature of delivering said isolated nucleic acid or peptide into nucleus of a tumor cell.

The invention also relates to a vector expressing an isolated peptide of the invention. The expression vector may be a plasmid.

In one embodiment, an isolated host cell comprises the expression vector of the invention.

In another aspect, the invention relates to use of an isolated nucleic acid, an isolated peptide, a vector, a conjugate or a complex of the invention in the manufacture of a medicament for treatment of a tumor in a subject in need thereof.

Alternatively, the invention relates to a method for treatment of a tumor in a subject in need thereof, comprising administering a therapeutically effective amount of an isolated nucleic acid, an isolated peptide, a vector, a conjugate or a complex of the invention to the subject in need thereof.

Further in another aspect, the invention relates to use of an isolated antibody or a binding fragment thereof specific for PSPC1 Tyr 523 phosphorylation (pY523) in the manufacture of a reagent kit for measuring the expression level of PSPC1 pY523 in a tumor sample from the subject in need thereof.

Alternatively, the invention relates to a method for predicting tumor progression, metastasis and prognosis of a subject with a tumor, comprising (i) providing an isolated antibody or a binding fragment thereof specific for PSPC1 Tyr 523 phosphorylation (pY523); and (ii) measuring the expression level of PSPC1 pY523 in a tumor sample from the subject with the tumor; wherein an absence or a decrease in the expression level of PSPC1 pY523 in nucleus compared to a control tissue sample indicates tumor progression, metastasis and poor tumor prognosis. The control tissue sample may be an adjacent normal tissue of non-tumor-bearing tissues.

In one embodiment, the use of the invention in the manufacture of the medicament for the treatment of the tumor in the subject in need thereof further comprises the use of the invention in the manufacture of the kit reagent for measuring the expression level of PSPC1 pY523 in the tumor sample from the subject in need thereof.

The use of the invention in the manufacture of the medicament for the tumor treatment may be after the use of the invention in the manufacture of the kit reagent for measuring the expression level of PSPC1 pY523 in the tumor sample, and vice versa.

The tumor sample is from a cancer patient or from a subject having a tumor.

Further in another aspect, the invention relates to a reagent kit for measuring the expression level of PSPC1 pY523 in a tumor sample, wherein the reagent kit comprises an isolated antibody or a binding fragment thereof specific for PSPC1 Tyr 523 phosphorylation (pY523).

The reagent kit may further comprise an instruction suggesting that an absence or a decrease in the expression level of PSPC1 pY523 in nucleus compared to a control tissue sample indicates tumor progression, metastasis and poor tumor prognosis.

In one embodiment, the isolated antibody is a polyclonal antibody.

In another embodiment, the polyclonal body may be raised by against a phosphopeptide comprising the amino acid residues CGGNFEGPNKRRRY (SEQ ID NO: 5) with the terminus Y being phosphorylated (Yp).

In one embodiment, the tumor is at least one selected from the group consisting of breast, lung, liver, leukemia, colon, prostate, ovary, cholangiocarcinoma, pancreatic, stomach, rectum, and esophageal cancer.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, explain the principles of the invention. Wherever possible, the same reference numbers are used throughout the drawings to refer to the same or like elements of an embodiment.

DETAILED DESCRIPTION OF THE INVENTION

Figure 1:
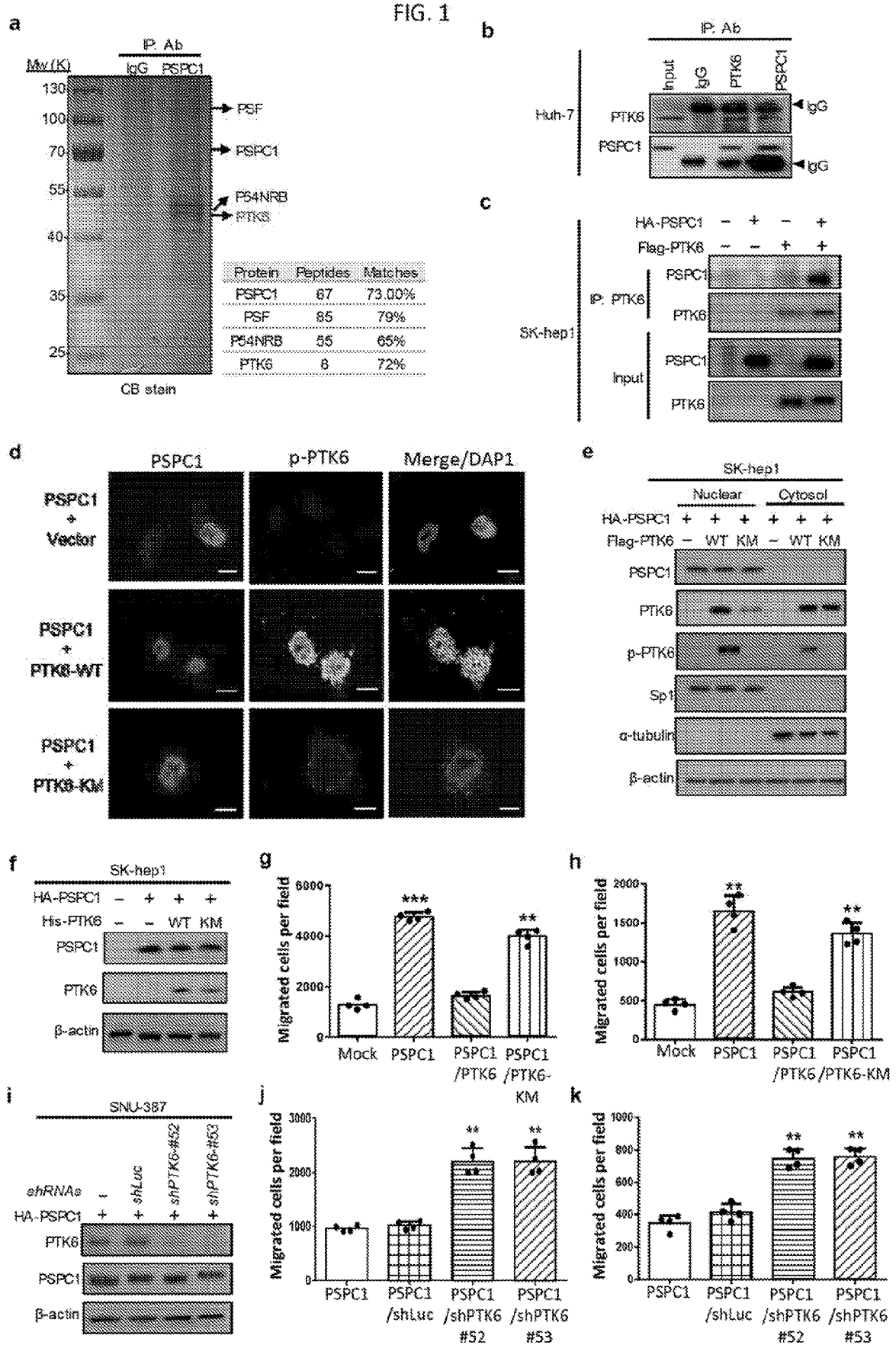
FIG. 1 shows phosphorylated-PSPC1 interacts with nuclear and tumor suppressive tyrosine kinase PTK6 led to inhibition of tumor progression. (a) Coomassie blue staining of the PSPC1 immunoprecipitated (IP) complex of Huh-7 cells lysates with anti-PSPC1 antibody separated by SDS-PAGE and subjected to LC-MS/MS analysis. Pre-immune IgG served as IP control and eight peptide sequences of PTK6 were identified. The percentage of peptide matches of the indicated proteins is shown. (b) Endogenous PSPC1 and PTK6 interaction analyzed by IP and Western blotting analysis in Huh-7 cells. Pre-immune IgG is the control and arrowhead is the IgG heavy chain. (c) Interaction of PSPC1 with PTK6 by ectopic expression of HA-tagged PSPC1 and/or Flag-tagged PTK6 protein in 293T cells by IP/western analysis. (d) Expressions of wild-type (WT), kinase-dead (KM) mutant and phosphor-form of flag-tagged PTK6 in SK-hep1 cells expressing HA-tagged PSPC1 by IF analysis. Colors of staining: PSPC1 (red), PTK6 (green) and nuclei (DAPI, blue). The scale bar represents 20 μm. (e) Subcellular distribution of wild-type (WT) and kinase-dead (KM) mutant of flag-tagged PTK6 in SK-hep1 cells expressing HA-tagged PSPC1 by Western blotting analysis. Sp1 and α-tubulin were used as internal controls for nuclear and cytoplasmic fractions, respectively. (f-h) SK-hep1 cells stably expressing HA-tagged PSPC1, His-tagged PTK6 wild-type (WT) or kinase dead (KM) mutant were analyzed by Western blotting analysis (f). Expression of PTK6, but not KM mutant of PTK6, suppressed PSPC1-mediated cell migration (g) and invasion (h) in SK-hep1. Data are represented as mean±SEM (n=4). (i-k) PTK6 knockdown by shRNAs (shRNA #52 and shRNA #53) and Western blotting analysis in SNU-387 cells expressing HA-tagged PSPC1 (i). PTK6 knockdown potentiated cell migration (j) and invasion (k) in SNU-387 cells. shLuc is a control shRNA targeting luciferase. Data are represented as mean±SEM (n=4). All data statistics based on: p<0.01 *p<0.001 by one-way ANOVA with Brown-Forsythe test.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

Unless otherwise defined, all technical and scientific terms used herein have the same meaning as commonly understood by one of ordinary skill in the art to which this invention pertains. In the case of conflict, the present document, including definitions will control.

As used herein "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "treating" or "treatment" refers to administration of an effective amount of the compound to a subject in need thereof, who has cancer, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$$\text{HED} = \text{animal dose in mg/kg} \times (\text{animal weight in kg/human weight in kg})^{0.33}.$$

The invention relates to the discovery that PSPC1 is a phosphorylation-dependent substrate of PTK6. PSPC1 directly interacts with PTK6 via phosphorylation-dependence, leading to suppression of EMT. CSC and metastasis. The invention also relates to the discovery of a PSPC1 C-terminal fragment with 131 amino acid residues as a therapeutic drug for suppressing tumorigenesis in HCC orthotopic model.

Nucleus-Targeted Drug Delivery

Techniques for cell nucleus drug delivery has been known in the art. For example, Deepthi A et al reported nuclear drug delivery within tumor cells ("Targeted Drug Delivery to the Nucleus and its Potential Role in Cancer Chemotherapy" J. Pharm. Sci. & Res. Vol. 5(2), 2013, 48-56). Cohen et al. reported a nuclear localization signal peptide ("Nucleus-targeted drug delivery: Theoretical optimization of nanoparticles decoration for enhanced intracellular active transport", Nano Lett. 2014 May 14; 14(5):2515-21). Jung et al. reported nucleus-targeting zwitterionic carbon dots ("Cell Nucleus-Targeting Zwitterionic Carbon Dots" Sci Rep. 2015; 5: 18807). Zhong J. et al. reported a smart polymeric platform for multistage nucleus-targeted anticancer drug deliver (Biomaterials. 2015 October; 65:43-55). Maity A et al. reported efficient subcellular targeting to the cell nucleus of quantum dots densely decorated with a nuclear localization sequence peptide (ACS Appl, Mater Interfaces 8, 3, 2001-2009).

The nucleotide and amino acid sequence information on PSPC1, its C-terminal 131 amino acid residues fragment, and PTK6 are as follows:

```
The amino acid sequence of human PSPC1-CT131
(SEQ ID NO: 1):
MGDMGPRGAINMGDAFSPAPAGNQGPPRMMGMNMNNRATIPGPP

MGPGPAMGPEGAANMGTPMMPDNGAVHNDRFPQGPPSQMGSPMG

SRTGSETPQAPMSGVGPVSGGPGGFGRGSQGGNFEGPNKRRRY
```

Nucleotide sequence of human PSPC1 cDNA (SEQ ID NO: 2); amino acid sequence of human PSPC1 (SEQ ID NO: 3); amino acid sequence of human PTK6 (SEQ ID NO: 4); GGNFEGPNKRRRY (SEQ ID NO: 8).

The invention relates to the discovery that PSPC1 upregulation is a contextual determinant of an oncogenic switch in which subcellular translocations of PTK6 to cytoplasm and β-catenin to nucleus. PSPC1-CT131 is a novel inhibitor which abrogates oncogenic functions of PSPC1 and tyrosine kinase PTK6 and interferes oncogenic subcellular translocation of PTK6 and β-catenin to suppress tumor progression in HCC models.

EXAMPLES

Exemplary instruments, apparatus, methods and their related results according to the embodiments of the present invention are given below.

Methods

Antibodies and cell Ones. Antibodies used were PSPC1 (Santa Cruz); Snail, Slug, Twist, Nanog, Oct4, Sox2, N-cadherin, E-cadherin, ZO-1, β-catenin, gamma-catenin; ZEB1; Vimentin Phospho-Smad2 (Ser465/467)/Smad3 (Ser423/425) and Smad2/3; (Cell Signaling Technology); β-actin, HA tag (Sigma); PTK6 and Phospho-PTK6 (Tyr 342)(Millipore); His tag (Qiagen); Brk, Sp1 and Twist (Proteintech Group Inc). Human hepatocellular carcinoma (HCC) cell lines SK-Hep1, Huh7, SNU-387, Mahlavu and human embryonic kidney cell line 293T and 293FT cells were maintained in low passage culture. SK-Hep1 labeled with firefly luciferase were established by lentivirus infection. The full-length PSPC1 cDNA was cloned into pcDNA3.0-HA plasmid. The PSPC1-CT131 was further cloned into pEGFP-C2 plasmid for confocal microscopy analysis. The expression plasmids of secreted form of PSCP1 wild-type and Y523F mutation cloned into pSecTag2A were purchased and synthesized from TOOLS (Taiwan) for SPR assay (Biacore). The expression plasmids of Nanog, Oct4, Sox2 and the promoter constructs of Snail, Slug, Nanog and Oct4 were purchased from Addgene 2. The Twist promoter plasmid was a gift from Dr. L. H. Wang (Taiwan).

MS Analyse. The IP-PSPC1 protein complexes were fractionated by SDS-PAGE, followed by instant blue Coomassie staining. The Coomassie-staining gel bands were manually cut, destained, and digested with trypsin. Proteins from Immuno-precipitation (IP) were fractionated by one-dimensional electrophoresis followed by trypsin in-gel protein digestion. The peptide mass and peptide fragment mass were measured by LC-ESI/MS/MS or 2D-LC-ESI/MS/MS, and the proteins identified by matching to NCBI and SwissProt databases.

Small hairpin RNA and lentiviral infections to cells. TRCN0000021552 (shRNA52) and TRCN0000199853 (shRNA53) as shRNA for PTK6 were obtained from the RNAi Core Facility Platform of Academia Sinica. pLKO.1 with shRNA, pMD.G and pCMV-ΔR8.91 were introduced into HEK293FT cells for lentiviral packaging. The viral supernatants were collected and used to infect HCC cancer cell lines. Control vector expressing shRNA against LacZ (pLKO.1-shLacZ) was used as a negative control.

RNA sequencing (RNA-Seq) and data analysis. Total RNAs were isolated from Mock control, PSPC1-overexpressing, PSPC1/PTK6-overexpressing, PSPC1-Y523F-overexpressing, and PSPC1-YS23F/PTK6-overexpressing SK-Hep1 cells, respectively. Mock control, PSPC1-CT131-overexpressing, and PSPC1-mutNLS-overexpressing cells in Mahlavu cells were extracted by Trizol reagent, respectively. RNA quality was examined by spectrophotometry, agarose gel electrophoresis (18S and 28S rRNA ratio) and Agilent Technologies 2100 Bio-analyzer with an RNA integrity number (RIN) value greater than 8. After rRNA depletion, RNA fragmentation and library preparation, the constructed libraries were performed 150 bp paired-end sequencing by an Illumina HiSeq 4000 sequencer at TOOLS (Taiwan). Expression analysis was performed, aligning to the hg18 genome build. FPKMs were quantile normalized across all samples.

RNA preparation and Quantitative Reversed Transcription PCR (RT-qPCR). Total cellular RNA was extracted using Trizol reagent for RT-PCR and quantitative RT-PCR was performed.

Subcellular fractionation and Western blotting. Nuclear and cytoplasmic fractions were prepared using Nuclear and Cytoplasmic Extraction reagents. Total cellular proteins were extracted by RIPA lysis buffer and then quantified by BCA protein assay kit. The protein lysates were separated on SDS-PAGE, electro-blotted onto PVDF membranes, probed with primary antibody followed by HRP-conjugated secondary antibody, and detected by enhanced chemiluminescence (ECL).

GST pulldown assay. The cDNA fragments for PSPC1 were cloned to pGEX-4T-1 vector to generate glutathione S-transferase (GST) fusion proteins and assays were performed using recombinant GST-PSPC1 and PTK6. For GST pulldown assay, GST-tagged PSPC1 were incubated with recombinant PTK6 in GST pulldown buffer (100 mM Tris [pH 8.0], 1% NP40, 150 mM NaCl) overnight at 4° C. and then washed six times. The bound proteins were analyzed by western blotting.

Immunofluorescence microscopy. Cells were plated onto glass coverslips, fixed with 4% paraformaldehyde, permeabilized by cold methanol and 0.1% TRITON®, stained with primary antibody then the corresponding Alexa Fluor-488 or Alexa Fluor-568-conjugated secondary antibody. The antibodies-labeled cells on coverslips were stained with 4', 6-diamidino-161 2-phenylindole (DAPI). Images were obtained by confocal laser-scanning microscopy. Serum-starved and confluent cultures of SK-Hep1 cells were used for detection of PSPC1, PTK6, γ-catenin and N-cadherin expression. Mahlavu cells were used for detection of EGFP, E-cadherin and N-cadherin expression.

Cell Migration and Invasion Assays. Cell migration assay was performed using Boyden chambers. For the invasion assay, each transwell was coated with MATRIGEL™. An upper insert containing $1\times10^4$ cells in 200 μl serum free medium was placed on the lower chamber filled with 800 μl complete medium as chemo-attractant. After 24 hours, cells were fixed with methanol for 10 minutes. Both MATRIGEL™-attached and un-migrated cells were removed using cotton swabs. The chambers were stained with Giemsa stain and migrated cells counted.

Immunohistochemistry. After deparaffinization, tissue sections were subjected to 10 mM citrate buffer (pH6.0) by microwave treatment for 20 minutes for antigen retrieval. The samples were immersed in 3% $H_2O_2$ for 30 min to block endogenous peroxidase, then incubated with anti-PSPC1, anti-PTK6 or anti-PSPC1 phospho-Y523 primary antibody diluted in blocking buffer at 4° C. overnight. The slides were processed using the SUPERPICTURE™ Polymer Detection kit, and counterstained with hematoxylin. Tissue arrays were purchased from SUPER BIO CHIPS. All IHC results were examined and scored from 1 to 4 based on their expression intensity by two independent pathologists and defined the intensity score above 3 as high-level protein expression. For association with patient survival, the score of expression intensity was multiplied by percentage of stained cells. High and low expression were defined by the Cutoff finder for the most significant grouping in association with patient survival. Usage of human cancer tissue arrays from commercial sources was approved by the Human Subject Research Ethics Committee/IRB of Academia Sinica. For preparing cell blocks from cell lines, $1\times10^6$ cells were re-suspended in 2% ultra-low gelling temperature (ULGT) agarose and then placed on ice until solid. The solid agar was further fixed with 4% paraformaldehyde and then embedded.

Spheroid Formation assays. 1,000 cells were suspended in DMEM/F12 medium containing 20 ng/ml EGF, 20 ng/ml basic FGF and B27 supplements. Cells with limiting dilutions were cultured in 12-well plates for 2 weeks. Spheroids larger than 20 μm were counted for spheroid-forming index.

Luciferase Reporter Assays. Luciferase activities of firefly and renilla were measured by DUAL-GLO® Luciferase Assay System.

Gene set enrichment analysis (GSEA). GSEA was performed on various gene signatures by comparing gene sets from MSigDB database or from published gene signatures. Gene sets with a false discovery rate (FDR) value <0.05 found by comparing the enrichment score to enrichment results generated from 1,000 random permutations were considered statistically significant.

Enzyme-linked immunosorbent assay (ELISA). Conditioned medium from each group was collected and stored at −80° C. prior to ELISA analysis. The concentrations of WNT1, WNT3A were measured by Human WNT1 and WNT3A ELISA kit. Total TGF-β1 was measured by Human TGF-beta1 Platinum ELISA kit.

Immunoprecipitation (IP). Cells were lysed with RIPA buffer. The primary antibody or control IgG with Protein A/G SEPHAROSE® Beads was added to the lysates and incubated at 4° C. for overnight. The beads were collected and washed with RPA buffer before immunoblotting.

Side population Detection. Cells were harvested and adjusted in fresh medium to $1\times10^6$ cells/mL. Aliquots were put aside for control purpose, and either verapamil (20-100 μM) or reserpine (20-100 μM) was added. Verapamil and reserpine are known to block several ABC drug transporters.

PSPC1 site-directed mutagenesis. The QUIKCHANGE® 11 mutagenesis kit was used to generate all PSPC1 mutants in a pCDNA3.0-HA plasmid. For cell line transfection experiments, JETPRIME® transfection reagent was used, and stable expressing clones were derived with G418 or zeocin selection for in vivo experiments. NLS mutant (R409A) and Y523F mutants were generated by digesting the corresponding parental plasmids and PCR amplification with the following primers:

```
Y523F-F:
                                      (SEQ ID NO: 6)
CCCTAATAAGCGTCGTAGATTTTAATCTAGAGGGCCCTATTC

Y523F-R:
                                      (SEQ ID NO: 7)
GAATAGGCCCTCTAGATTAAAATCTACGACGCTTATTAGGG
```

Protein 3D structure prediction. The sequences of PSPC1 and PTK6 were retrieved from NCBI database. Protein structure prediction was performed by using I-TASSER. The structures with best scores were chosen for further analysis. The protein-protein docking predictions were performed by using ClusPro.

Establishment of an orthotopic tumor model for hepatocellular carcinoma. Six to eight weeks old male Swiss nu/nu mice were housed and maintained under specific pathogen-free conditions. All mouse experiments were conducted with approval from the Experimental Animal Committee, Academia Sinica. Cells were re-suspended ($1 \times 10^6$ cells/0.05 mL HBSS) and injected into the liver. Lung metastasis and primary liver tumor growth were measured at week 20 after implantation or at time of sacrifice. Lung metastasis and primary liver tumors were monitored by bioluminescent imaging using IVIS image system. Mice were killed for examining lung metastasis and primary liver tumors.

In vivo metastasis assay. For systemic metastasis assay, the lung metastasis model was established by tail-vein injection of Mahlavu ($1.0 \times 10^6$/μL cells) cells into each 6-8-week-old male NOD/SCID mice in groups of eight mice. Lung metastatic signals were detected by using the IVIS system with the excitation and emission wavelength at 570 and 620 nm. The mice were sacrificed at 16-20 weeks after injection and the lungs were removed and fixed in 4% paraformaldehyde. The detectable tumor nodules on the surface of whole lung were counted for metastatic index. Histological staining was used to further confirm the presence of lung metastases.

PSPC1-CT131 plasmid administration. Solutions of PSPC1-CT131 plasmid and vehicle negative control were each diluted with 10% (wt/vol) glucose in in vivo-JETPEI®. All solutions were mixed by vortexing for 10 s and incubated for at least 15 min at 37° C. before injection. Each mouse received either glucose (200 μl) in the control group, or oligonucleotide (oligonucleotide 100 μl plus saline 100 μl) in the treatment group through tail vein injection consecutively for 3 days and 3 additional injections were performed once a week for the following 8 weeks. Two additional groups of control animals were included: one consisting of untreated animals and the other of animals receiving a mixture of in vivo-JETPEI® solution containing 10% (wt/vol) glucose without added oligonucleotide.

Xenograft. Six-week-old female BALB/c nude mice were maintained under specific pathogen-free conditions. To establish a subcutaneous xenograft model, Mahlavu cells and Mahlavu cells plus PSPC1-CT131 plasmid suspensions were prepared at a concentration of $1 \times 10^7$ cells/ml, mixed with MATRIGEL™, and injected into mice subcutaneously. Tumor incidence were monitored at seven weeks after injection (n=5). Statistical test was performed by two-way ANOVA with post-hoc Tukey's test. The data represent the mean±SD.

Generation of Phospho-specific antibody p-Tyr523-PSPC1. Rabbit polyclonal antibodies against phospho-Tyr523 of PSPC1 were raised against the phosphopeptide CGGN-FEGPNKRRR(Yp)(SEQ ID NO: 5, where Tyr is phosphorylated) synthesized by LTK Biolaboratories. Rabbit inoculation and crude serum production were performed by LTK Biolaboratories. Antibodies were affinity-purified on a phosphopeptide column. The eluted antibodies were purified by passing them through an un-phosphorylated peptide column to remove antibodies that cross-react with un-phosphorylated epitopes.

In vitro kinase assay. The kinase activity was measured using ADP-Glo kinase Assay Kit: BRK Kinase Assay with PSPC1 phospho-peptide as a substrate to compare the activity of phosphopeptide or nonphosphopeptide with BRK. The luminescence was measured (n=3) using a luminometer plate reader.

Statistical and Kaplan-Meier Survival Analysis. Data were expressed as the mean±SD. Statistical analyses were conducted using GraphPad Prism 7.0 statistical software. *$P \leq 0.05$, $P \leq 0.001$ and *$p \leq 0.0001$ by two-tailed Student's t-test and one-way ANOVA. Survival durations were analyzed using the Kaplan-Meier method and compared by the log-rank test in patient groups.

Results

Phosphorylated-PSPC1 Interaction with Nuclear Tyrosine Kinase PTK6 Causes Inhibition of Tumor Progression PSPC1-interacting complexes were purified by immunoprecipitation (IP) and subjected to LC-MS/MS analysis (FIG. 1a). Endogenously or ectopically expressed PSPC1 and PTK6 interacts in HCC cells (FIGS. 1b, c). It was found that the interaction of PSPC1 and PTK6 was tyrosine phosphorylation-dependent. The kinase dead mutant of PTK6 (PTK6-K219M or PTK6-KM) or phosphatase treatment diminished tyrosine phosphorylated proteins and abolished PSPC1/PTK6 interaction and the enrichment of active PTK6 (pY342) is most apparent at the nucleus where PSPC1 is overexpressed (FIG. 1d). Subcellular fractionation assay further supports that PSPC1 interacted with active nuclear PTK6 but not cytoplasmic PTK6-KM mutant. (FIG. 1e). Mapping of PSPC1/PTK6 interacting domains indicated that PSPC1 C-terminal proline-rich domain and the PTK6 SH2 and SH3 domains are essential.

The impact of PSPC1/PTK6 interaction on motility of HCC cancer cells was investigated. PTK6 but not PTK6-KM mutant diminished PSPC1-enhanced cell migration and invasion in SK-hep1 cells (an HCC cell line with indigenous knock-out of PSPC1 and low expression of PTK6)(FIGS. 1f-h). PTK6 knockdown with short hairpin RNAs (shPTK6-#52 and -#53) in SNU-387 (expressing relatively low level of PSPC1 but high level of endogenous PTK6) abolished PTK6-suppressed PSPC1-enhanced cell migration and invasion (FIGS. 1i-k). This suggests that PSPC1 is a substrate of nuclear PTK6 that reduced PSPC1-enhanced tumor progression in HCC cells.

Figure 2:
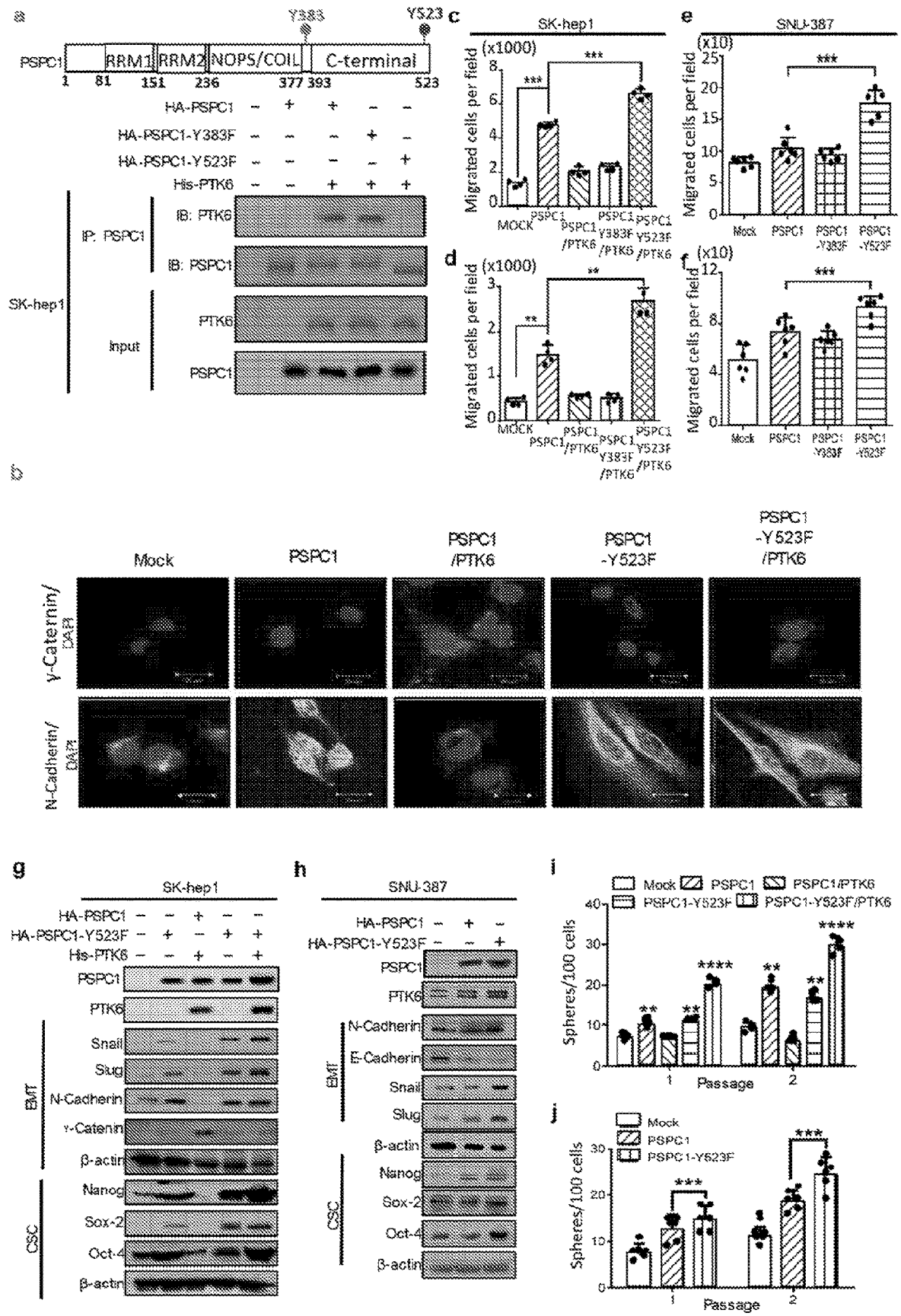
FIG. 2 shows PSPC1 upregulation and PSPC1-Y523F mutant release PTK6 nuclear sequestration to synergize PSPC1 and cytoplasmic PTK6 oncogenic effects. (a) Mutation of PSPC1-Y523F but not PSPC1-Y383F abolished PSPC1/PTK6 interaction by IP/western blotting analysis (Bottom). (Top) A cartoon to illustrate domain structures and tyrosine amino acid residues Y383 and Y523 at C-terminal of PSPC1 protein. (b) Analysis of cell morphology in 2D (phase) and 3D (spheroids) culture and expression of epithelial (γ-catenin) and mesenchymal markers by IF in divergent PSPC1/PTK6 transfectants in SK-hep1 cells. Colors of staining: γ-catenin (red), N-cadherin (green) and nuclei (DAPI, blue). The scale bar represents 20 μm. (c-d) PTK6 suppressed PSPC1-enhanced cell migration (c), invasion (d), in SK-hep1 cells. Mutation of PSPC1-Y523F but not Y383F abolished PSPC1-enhanced cell migration and invasion. Data are represented as mean±SD (n=4). (e-f) SNU387 expressing a high level of PTK6 reduced PSPC1 or PSPC1-Y383F mediated cell migration (e) and invasion (f), but not PSPC1-Y523F. Data are represented as mean±SD (n=4). (g) PTK6 suppressed PSPC1-potentiated EMT and cancer stemness (CSC) in western blotting analysis containing EMT and CSC markers in SK-hep1 cells. (h) SNU387 expressing a high level of PTK6 reduced PSPC1-mediated oncogenic effects but did not reduce PSPC1-Y523F mutant mediated oncogenic effects. PSPC1-Y523F mutation potentiated expression of EMT and CSC markers but reduced expression of E-cadherin in SNU-387 cells by western blotting analysis. (i) PTK6 suppressed PSPC1-enhanced cell spheroids formation in SK-hep1 cells. PSPC1-Y523F but not Y383F mutant abolished PSPC1-enhanced spheroids formation with series dilutions in 20 days cultures. Data are represented as mean±SEM (n=6). (j) SNU387 expressing a high level of PTK6 reduced PSPC1 mediated oncogenic effects but did not reduce PSPC1-Y523F. PSPC1-Y523F mutation potentiated spheroids formation with series dilutions for 20 days cultures. Data are represented as mean±SEM (n=6). All data statistics based on: *p<0.05, p<0.01 *p<0.001 by one-way ANOVA with Brown-Forsythe test.

PSPC1 Upregulation and PSPC1-YS23F Release of PTK6 Nuclear Sequestration Synergize PSPC1 and Cytoplasmic PTK6 Oncogenic Effects There are two conserved tyrosine residues Y383 and Y523 in PSPC1 (FIG. 2a, top panel). Protein 3D structures were simulated with wild-type PSPC1, PSPC1-Y383F and PSPC1-Y523F for prediction of PTK6 phosphorylation-mediated alteration of PSPC1-pro-metastatic capabilities. The PSPC1 Y383F and Y523F mutations have similar protein structural folding as compared to wild type. The YS23 (PSPC1-Y523F), but not the Y383 (PSPC1-Y383F) was the major PTK6 phosphorylation site (FIG. 2a) and essential for PSPC1/PTK6 interaction, cell migration and invasion in SK-hep1 cells (FIGS. 2c, d). Loss of PTK6 interaction by expression of PSPC1-Y523F showed additional oncogenic effects including elongated fibroblast-like and scattered morphology in 2D culture, compacted and numerous spheroids in 3D culture, increased expression of N-cadherin (a mesenchymal marker) but decreased expression of γ-catenin (an epithelial marker) in SK-hep1 cells (FIG. 2b).

PSPC1 upregulation induced EMT-TFs (SNAIL and SLUG) promoter activity and expression of high protein levels of the EMT-TFs and CSC-TFs (NANOG, SOX2 and OCT4). Expression of PSPC1-Y523F/PTK6 constructs in SK-hep1 (FIG. 2g) and SNU-387 cells (FIG. 2h) increased expression of EMT-TFs and CSC-TFs. Adding up oncogenic effects of PSPC1-Y523F/PTK6 as compared with wild-type PSPC1 was further validated in SNU-387 cells which expressed high endogenous levels of PTK6 (FIGS. 2e, f, h). PSPC1-Y523F/PTK6 increased, but PSPC1/PTK6 decreased, tumor sphere formation even in the second passage stage in SK-hep1 (FIG. 2i) and SNU-387 cells (FIG. 2j), suggesting that PTK6 reduced PSPC1-mediated self-renewal capacity which was reversed by loss of PSPC1/PTK6 interaction. Sternness feature was validated by detecting the presence of side population cells. Verapamil is an inhibitor of ABC transporter proteins required for Hoechst33342 efflux. SP cells with a low Hoechst33342 fluorescence intensity were detected in PSPC1/PTK6 expressing cells isolated from SK-hep1. The proportion of the SP cells present in the PSPC1-Y523F/PTK6-transfected SK-hep1 cells was elevated. This suggests that PSPC1 upregulation and PSPC1-Y523F mutation both can synergize PSPC1 and cytoplasmic PTK6 oncogenic effects by reducing PTK6 nuclear sequestration, which leads to tumor migration ability.

PSPC1 Upregulation and PSPC1-Y523F Mutant Synergize Nuclear PSPC1/β-Catenin Interaction, Cytoplasmic PTK6 Oncogenic Effects and Autocrine Wnt/β-Catenin Signaling.

Figure 3:
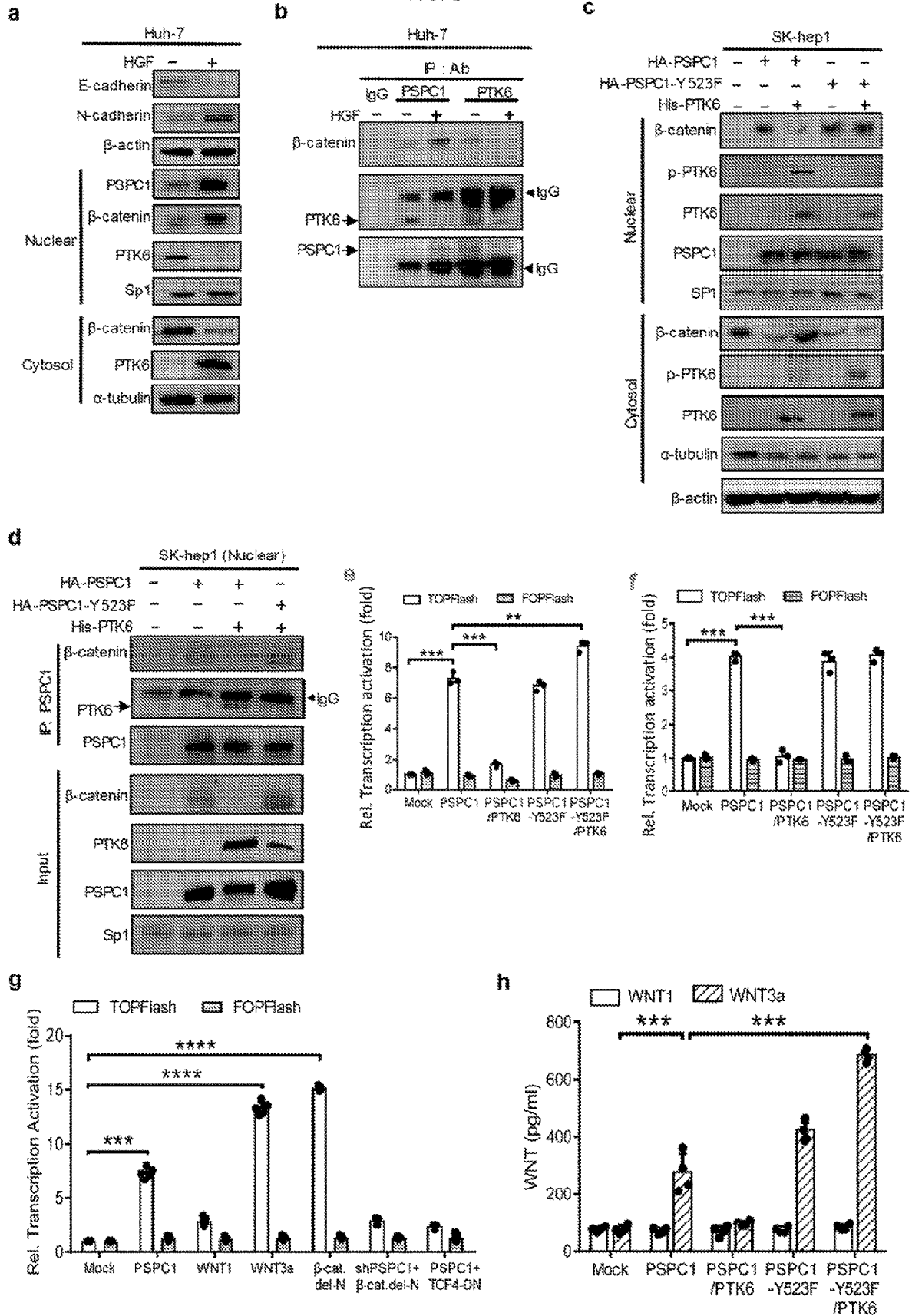
FIG. 3 shows dynamic interactions of PSPC1, PSPC1-Y523F and PTK6 modulate Wnt/βcatenin signaling. (a-b) Huh-7 treated with or without HGF (10 ng/ml) for EMT induction. Under HGF stimulation, nuclear PSPC1 interacted with β-catenin and loss of PTK6 interaction owing to an increase of cytosolic PTK6 accumulation in HGF-induced EMT model in IP/western blotting analysis. Arrowhead is the IgG heavy chain. Arrows are indicated proteins after IB. (c) Nuclear (SP1 as marker) and cytosolic (α-tubulin as marker) localization of PSPC1/PTK6 interaction and β-catenin analyzed by western blotting analysis in SK-hep1 cells. PSPC1-Y523F mutant further enhanced nuclear localization of β-catenin. (d) Nuclear (SP1 as marker) localization of PSPC1/PTK6 interaction and βcatenin analyzed by IP/western blotting analysis in SK-hep1 cells. Y523F PSPC1 mutant further enhanced nuclear interaction with β-catenin but not PTK6. (e) Relative transcription activation of TCF4 luciferase promoter reporter assay with TOP-Flash or FOP-Flash expressing divergent PSPC1/PTK6 constructs in SK-hep1 cells expressing vector alone (Mock), HA-tagged PSPC1, HA-tagged PSPC1 plus His-tagged PTK6, HA-tagged Y523F mutant or HA-tagged Y523F mutant plus His-tagged PTK6 proteins. Data represents the mean±SEM (n=3). (f) Relative transcription activation LEF1 luciferase promoter reporter assay with TOP-Flash or FOP-Flash in SK-hep1 cells expressing vector alone (Mock), HA-tagged PSPC1, HA-tagged PSPC1 plus His-tagged PTK6, HA-tagged Y523F mutant or HA-tagged Y523F mutant plus His-tagged PTK6 proteins. Promoter activation (fold) was calculated relative to vector alone (Mock) in cells. Y523F further potentiated PSPC1-mediated transcription activity of TCF4 but not LEF1 promoter reporter assays. Data represents the mean±SEM (n=3). g PSPC1 potentiated Wnt/β-catenin autocrine signaling by activation of TOP-Flash reporter and FOP-Flash was used as negative control in 293T cells with co-transfection of HA-PSPC1, Wnt3a, β-catenin del-N(deletion of N-terminal) PSPC1 shRNA (shPSPC1), TCF4-DN (dominant negative) or combinations as indicated (g) Data represents the mean±SEM (n=3). (h) Secreted cytokines Wnt1 and Wnt3a protein expression measured by ELISA assays of conditional medium after transfection of divergent PSPC1/PTK6 expression constructs in SK-hep1 cells. Data represents the mean±SEM (n=3). *p<0.05, p<0.01, *p<0.001 by one-way ANOVA with Brown-Forsythe test.

Huh-7 cells with high endogenous expression of PTK6 were stimulated with hepatocyte growth factor (HGF) for induction of cancerous EMT microenvironment as evidenced by reduced expression of epithelial marker E-cadherin and increased expression of N-cadherin (FIG. 3a). HGF stimulation increased nuclear expression of PSPC1 and β-catenin and reduced the expression of nuclear PTK6. In contrast, expression of cytoplasmic β-catenin was decreased whereas cytoplasmic PTK6 was increased (FIG. 3a). The HGF stimulation increased expression of nuclear β-catenin and cytoplasmic PTK6, potentiating the PSPC1/β-catenin interaction but diminishing PSPC1/PTK6 interaction (FIG. 3b). Expression of PSPC1-Y523F reduced nuclear p-PTK6 expression and caused β-catenin nuclear translocation (FIG. 3c). Over-expressed PSPC1-Y523F interacted with nuclear β-catenin, but not nuclear PTK6, which could explain the synergistic oncogenic effects of PSPC1-Y523F and cytoplasmic PTK6 in SK-hep1 cells (FIG. 3d).

TOP-Flash/FOP-Flash luciferase promoter assays were performed for evaluating the Wnt/β-catenin transcription activation. Overexpression of wild-type PSPC1, PSPC1-Y523F and PSPC1-Y523F/PTK6 in SK-hep1 cells activated TCF4/LEF1 of oncogenic Wnt/β-catenin signaling pathways, respectively. Overexpression of PTK6 inhibited the effects of wild type PSPC1 but not PSPC1-Y523F mutant in activating the transcription of TCF4/LEF1 (FIG. 3e, f). Overexpression of wild-type PSPC1, Wnt3a but not Wnt1, and constitutively active β-catenin (β-catenin del-N mutant) activated TCF4/LEF1 promoters of oncogenic Wnt/β-catenin signaling pathways, respectively. PSPC1 knockdown (shPSPC1) and dominant-negative TCF4 (TCF-DN), which prevent TCF4 binding to β-catenin, both abrogated the effects of PSPC1 in activating the transcription of TCF4/LEF1 (FIG. 3g).

Overexpression of PSPC1, PSPC1-Y523F and PSPC1-Y523F/PTK6 increased secreted Wnt3a but not Wnt1 protein in the conditioned medium of SK-hep1 transfectants. Overexpression of PTK6 inhibited the wild type PSPC1 but synergized the PSPC1-Y523F mutant activity in increasing Wnt3a secretion (FIG. 3h).

PSPC11PTK6/β-Catenin Axis is Necessary for Tumor Growth and Metastasis

Figure 4:
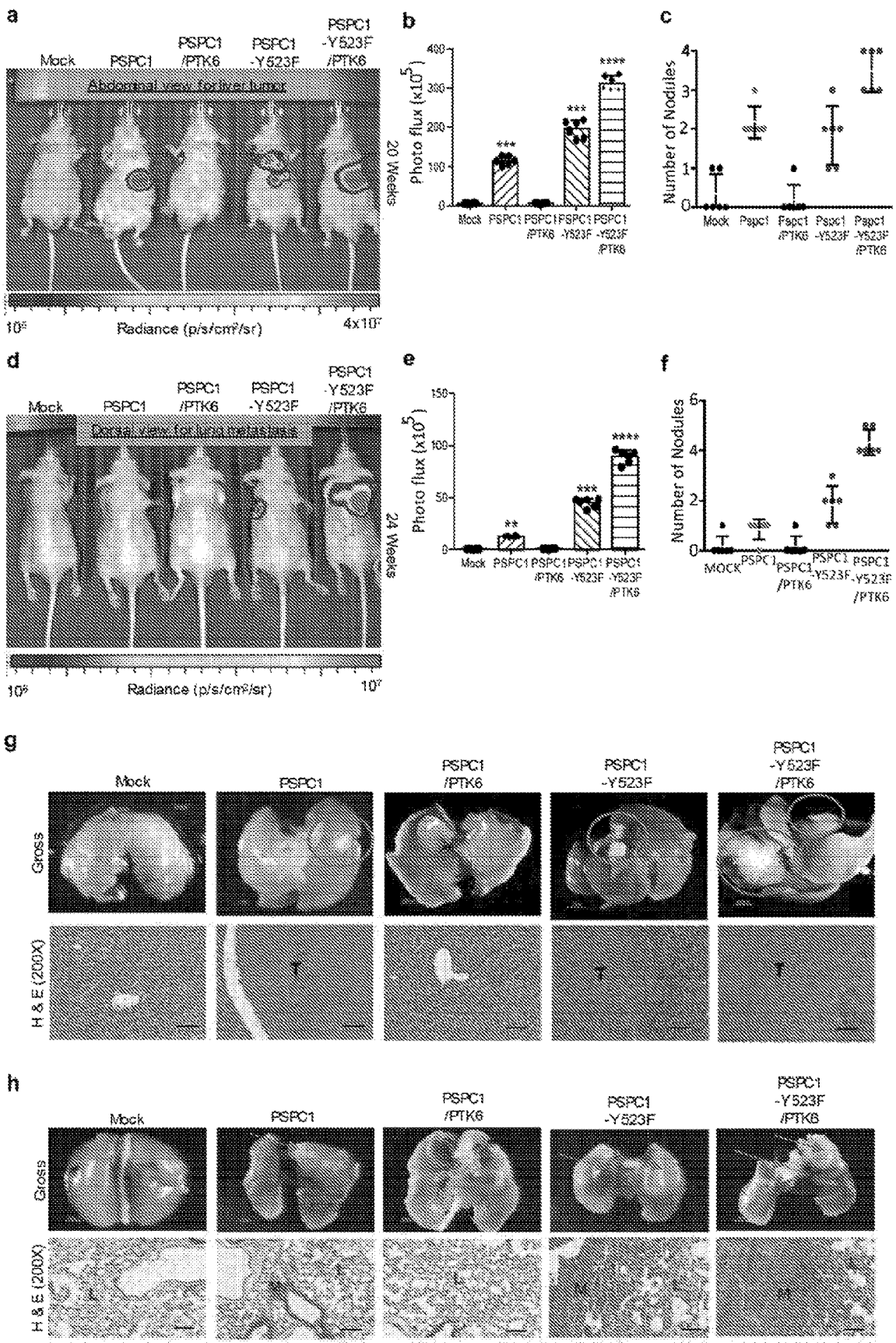
FIG. 4 shows PSPC1/PTK6/β-catenin axis is critical for tumor growth and metastasis in HCC. (a-f) Tumorigenesis (abdominal view for measuring liver tumors, a-c) and metastasis (dorsal view for measuring lung metastatic tumor, d-f) in orthotopic mouse HCC model bearing SK-hep1-luciferase cell transfectants by bioluminescence imaging (a and d), intensity of photo flux (b and e) and numbers of nodules in 20-week tumors (c and f). Data represent mean±SEM (n=6/group). PSPC1Y523F mutant enhanced tumorigenesis and metastasis compared to PSPC1 transfectant. p<0.01, *p<0.001, ****p<0.0001 by one-way ANOVA with Bartlett's test. (g-h) Representative images of liver and lung showing tumorigenesis and metastasis in hematoxylin and eosin-stained images. The circles indicate the locations of primary tumor nodules; The arrows indicate lung metastasis nodules; T, tumor; L, lung; M, metastasis. The scale bar represents 100 μm.

An orthotopic HCC tumor model was established by injection of SK-hep1/Luc cells transfected with various constructs into the liver. Tumor growth was measured at 6 weeks after tumor implantation and until 20 weeks. Luciferase intensity was measured by bioluminescence imaging (BLI). The of PTK6 showed tumor suppressive effects and PSPC1-Y523F/PTK6 showed extensive oncogenic effects (FIGS. 4a-c). The BLI intensity and number of tumor nodules metastasized to lungs significantly increased in mice bearing PSPC1-Y523F and PSPC1-Y523F/PTK6 tumors as compared with those bearing PSPC1 alone (FIGS. 4d-f). Primary liver tumor nodules and lung metastases were confirmed histologically (FIGS. 4g, h). Immunohistochemistry (IHC) staining of primary and metastatic tumors bearing PSPC1 and PTK6 for E-cadherin, vimentin, β-catenin and c-Myc showed significantly decreased levels of vimentin, β-catenin and c-Myc in vivo. Mice bearing PSPC1-Y523F/PTK6 tumors showed enhanced expressions of vimentin, β-catenin and c-Myc in their metastasized lung tumors as compared to those bearing PSPC1-Y523F tumors.

Expression of Phospho-Y523 PSPC1 and Unclear PTK6 is Associated with a Better HCC Patient Prognosis.

Figure 5:
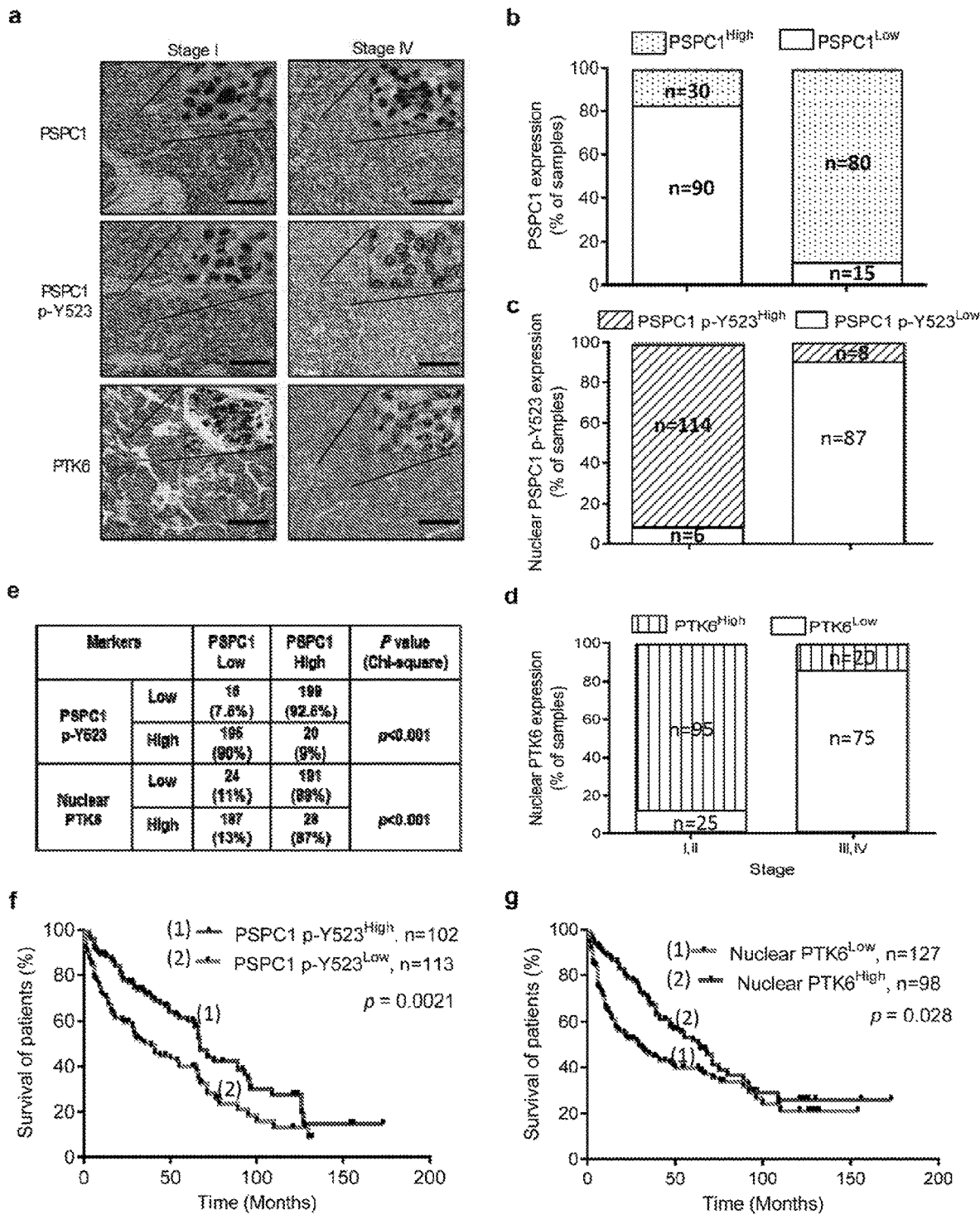
FIG. 5 shows expression of PSPC1-Y523 phosphorylation in human HCC tumor tissues as a favorable biomarker for cancer patient survival. (a) Representative IHC staining images for PSPC1, phospho-PSPC1 Y523 and PTK6 in low and high stages of human HCC tissues. The area marked by a small rectangle was enlarged and shown on the top right corner marked by a large rectangle in each IHC image. The scale bar represents 50 μm. (b-d) Expressions of PSPC1, phosphorylated-Y523 PSPC1 in nucleus, and nuclear PTK6 in early (I and II) and late stage (III and IV) tumors in human HCC tissues. Data are shown as mean percentage of samples, n=215. (e) The relationship between PSPC1 expression and the expression of phopho-PSPC1 Y523 and nuclear phospho-PTK6 in human HCC tissues. (f-g) Kaplan-Meier plot analysis of overall survival of 215 HCC patients on basis of low or high expression level of phospho-Y523 PSPC1 (f) and nuclear PTK6 (g), P value was determined by Gehan-Breslow-Wilcoxon test.

To demonstrate PSPC1-Y523 phosphorylation is of clinical relevance, a phospho-Y523 PSPC1-specific polyclonal antibody was generated. Immunohistochemistry (IHC) assays were performed on 215 human HCC tissue samples (FIG. 5a). PSPC1 expression was higher (H-score with discriminatory score exceeding 200) at late (III and IV) stages compared to earlier (I and II) stages (FIG. 5b). Nuclear expression of p-Y523-PSPC1 (FIG. 5c) and nuclear PTK6 (FIG. 5d) were higher in earlier stages as compared to late stages of HCC tumors. The increase in phospho-Y523-PSPC1 expression was correlated with augmented expression of nuclear PTK6 and associated with lower expression of PSPC1 in tumors (FIG. 5e). Higher expression of phospho-Y523-PSPC1 and nuclear PTK6 were associated with better survival rates as compared to lower expression of either one using Kaplan-Meier analysis (FIG. 5f, g, P=0.0021 and P=0.028, respectively). These results demonstrated that the expression level of phosphor-Y523 PSPC1 may be used as a prognostic biomarker.

Figure 8:
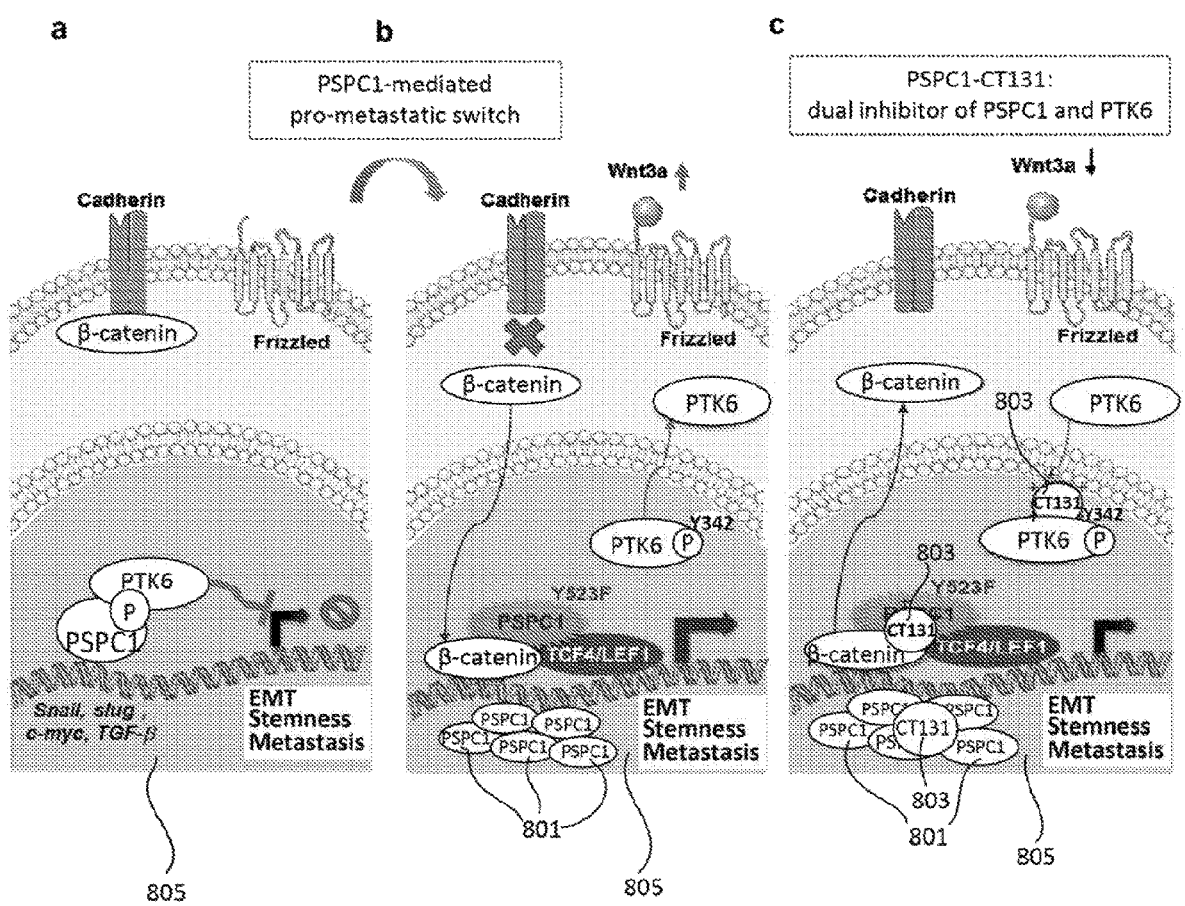
FIG. 8 are cartoons showing that PSPC1/PTK6 interaction modulates Wnt/β-catenin autocrine signaling and a PSPC1-CT131 fragment blocks PSPC1 and PTK6 signaling. (a) Phosphorylated-PSPC1 interacts with nuclear PTK6, leading to inhibition of tumor progression. (b) PSPC1 upregulation and PSPC1-Y523F mutant release PTK6 nuclear sequestration to synergize PSPC1 and cytoplasmic PTK6 oncogenic effects to modulate Wnt/β-catenin signaling. (c) A PSPC1-C-terminal 131 fragment acts as an inhibitor of oncogenic PSPC1 and PTK6 and reduces tumor metastasis in HCC.

Normally, PSPC1 is the substrate of nuclear PTK6 which suppresses PSPC1-mediated tumor progression. When PSPC1 is upregulated, it could collaborate with other cofactors such as nuclear β-catenin to exile nuclear PTK6 to the cytoplasm. The cytoplasmic PTK6 is oncogenic, facilitates Wnt3a autocrine signaling and causes HCC tumor progression (FIGS. 8a, b).

PSPC1-C-Terminal 131 Fragment is an Inhibitor of Both PSPC1 and PTK6

Figure 6:
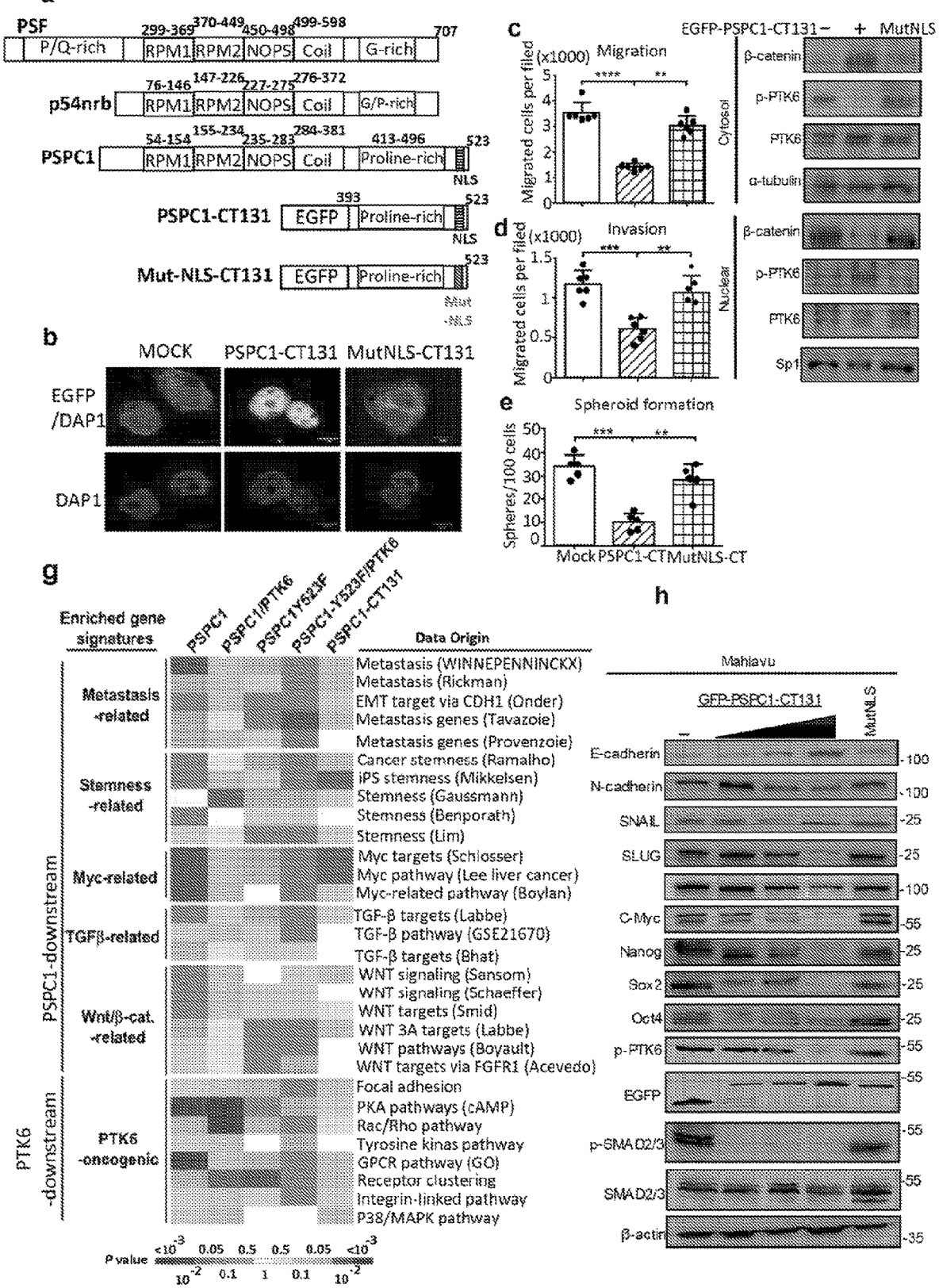
FIG. 6 shows PSPC1-C-terminal 131 fragment is an inhibitor of oncogenic PSPC1 and PTK6. (a) Protein fragments of PSPC1. (b) Expression and subcellular localization of EGFP-conjugated PSPC1-CT131 and nuclear localization sequence (NLS) mutant of PSPC1-CT131 (MutNLS-CT131) in Mahlavu cells, respectively. (c-e) Expression of PSPC1-CT131 but not MutNLS-CT in Mahlavu cells suppressed cell migration (c), invasion (d) and spheroids formation (e). Data represents the mean±SEM (n=6). *p<0.05, p<0.01 *p<0.001 by one-way ANOVA with Brown-Forsythe test. (f) Expression of PSPC1-CT 131 but not MutNLS-CT 131 altered subcellular localization of PTK6, p-PTK6 and β-catenin, and diminished PSPC1 by western blotting analysis in Mahlavu cells. (g) Comparison of PSPC1 and PTK6 downstream gene set signatures after transcriptome analysis (GSE114856) of PSPC1, PSPC1Y-523F, PSPC1-Y523F/PTK6, and PSPC1-CT131 in SK-hep1 cells and PSPC1CT131 in Mahlavu cells. (h) Western blotting analysis indicated that expression of EGFP-PSPC1-CT induced upregulation of E-cadherin, diminished expression of N-cadherin, Snail, Slug, Nanog, Oct4, p-PTK6, γ-catenin and c-myc in a dose dependent manner. MutNLS-PSPC1-CT expression did not alter expression of aforementioned proteins.

The C-terminal fragment of PSPC1 (PSPC1-CT131) is an inhibitor of both PSPC1 and PTK6. The PSPC1-CT131 fragment suppresses synergized oncogenic signaling because of its unique proline-rich interacting domain, which targets PSPC1 and SH3 domain of PTK6 as shown in molecular docking experiments. The constructs PSPC1-CT131-EGFP and its NLS mutant MutNLS-CT131 were generated and expressed. PSPC1-CT131 expressed in the nucleus (FIG. 6b), reduced cell migration, invasion and spheres formation (FIGS. 6c-e), and decreased expressions of cytosolic p-PTK6 and nuclear β-catenin (FIG. 6f) in Mahlavu cells. The Mahlavu cell line has high endogenous levels of PSPC1 and PTK6. Expression of MutNLS-CT in the cytoplasm failed to cause mesenchymal to epithelial phenotype conversion, thus turning off reciprocal subcellular translocation of p-PTK6 and β-catenin (FIG. 6f). Expression of PSPC1-CT131 but not MutNLS-CT131 in Mahlavu cells suppressed expression of secreted autocrine pro-metastatic ligands Wnt3a and TGF-β1. The results demonstrate that PSPC1-CT131 interacts with PSPC1 and nuclear p-PTK6 but not cytosolic p-PTK6 to block p-PTK6 subcellular translocation and abolish synergistic PSPC1/PTK6/β-catenin axis-mediated tumor progression.

RNA sequencing (RNA-Seq) of transcriptome (GSE114856) was performed followed by comparing gene signatures of gene sets enrichment analysis (GSEA) from divergent PSPC1/PTK6 construct transfected HCC cells. Thirty tumor progression-enriched gene signatures downstream of PSPC1 and PTK6 signaling pathways were selected, demonstrating significant up-regulation and down-regulation of gene expression under PSPC1/PTK6 interaction and PSPC1-CT131 treatments. Expression of the tumor progression genes related to metastasis-, stemness-, C-Myc-, TGF-β1, Wnt/β-catenin- and oncogenic PTK6-pathways were significantly upregulated in cells expressing constructs of PSPC1, PSPC1-Y523F, and PSPC1-Y523F/PTK6 (FIG. 6g). Expression of the tumor progressive genes in PSPC1/PTK6 and PSPC1-CT131-treated HCC cells were significantly down-regulated (FIG. 6g). The down-regulation of the oncogenic core proteins such as EMT-TFs, CSC-TFs, C-myc, β-catenin, TGF-β, PSPC1 and p-PTK6 by treatment with PSPC1-CT-131 but not MutNLS was dose-dependent in western blots (FIG. 6h).

Xenograft tumors were established by injection of parental or PSPC1-CT131 overexpressing Mahlavu cells. After 4-5 weeks of tumor growth, mice injected with PSPC1-CT31 overexpressing cells showed significantly decrease in tumor growth compared to the parental group. Mice bearing PSPC1-CT131 overexpressing cells had smaller tumor volumes than those bearing Mahlavu parental cells (P<0.001), suggesting inhibition of tumor growth by PSPC1-CT131 treatments (FIG. 7a).

Figure 7:
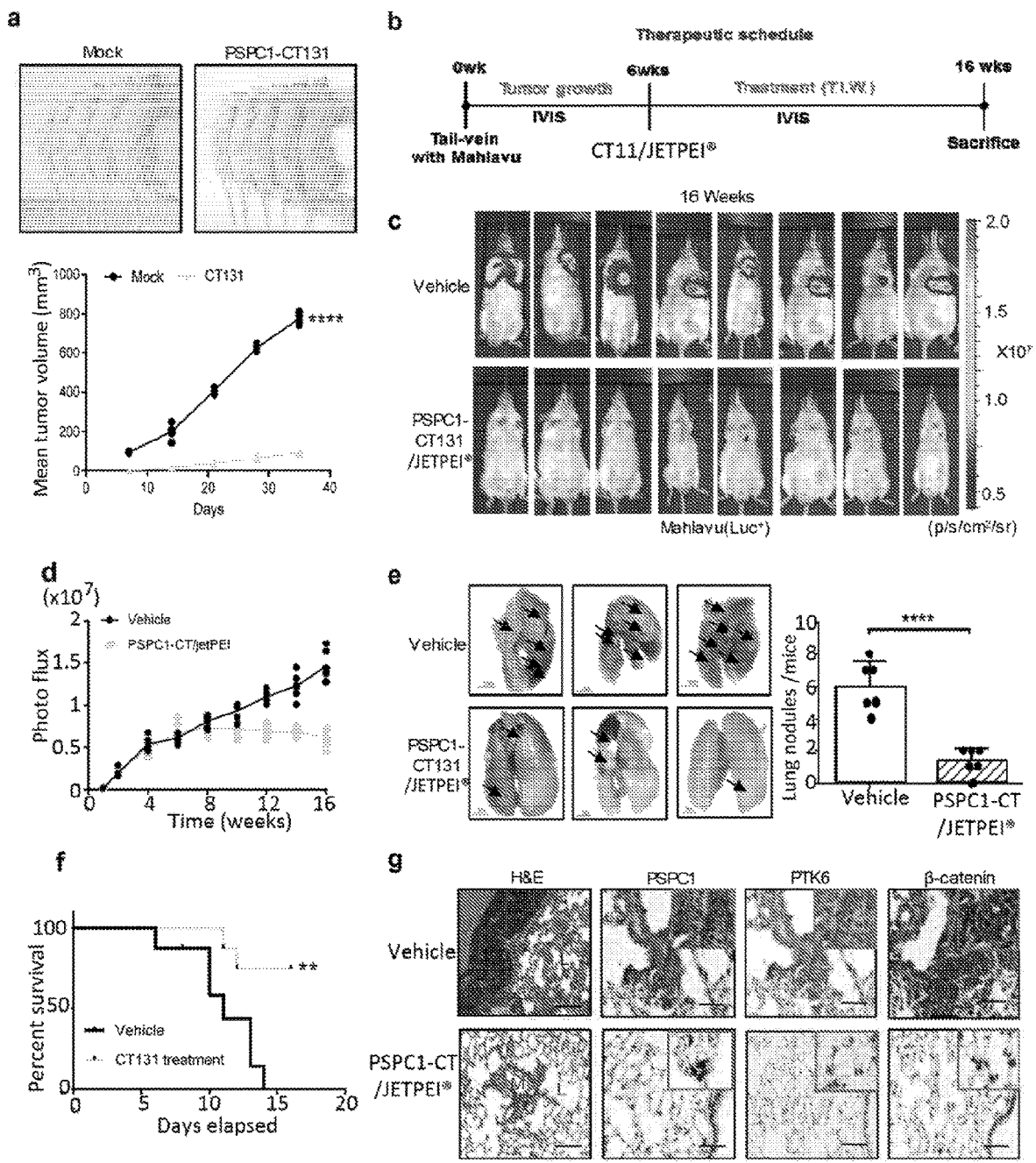
FIG. 7 shows that pharmacological targeting of PSPC1 and PTK6 reduces tumor metastasis in HCC. (a) Photographs of representative nude mice injected with Mahlavu parental cells or PSPC1CT131 overexpressing cells (top panel), and tumor size curves (bottom panel). Tumor volumes were measured at 6 weeks post injection. Data are represented as the mean±SEM (n=5/group). Statistical significance was determined by two-way ANOVA with post-hoc Tukey's test. ****P<0.001. (b) The schedule indicates the time when mice were injected via tail with vehicle or PSPC1CT131/JETPEI® transfected Mahlavu cells. (c) Representative bioluminescence imaging of FIG. 7b. (d-f) Injection of PSPC1-CT131 plasmid packaged in JETPEI® not only reduced lung metastasis (d and e) but also prolonged survival (f) in tail-vein injected lung metastasis model (n=8/group). P value was determined by Log-rank test. (g) IHC staining of lung tumors in the lung metastasis mouse model. Red tangles stands for enlargement of stained tissues placed on top right corner of each IHC images. An enlarged area is shown on the top right corner in each IHC image. The scale bar represents 100 μm.

PSPC1-CT131 plasmid packaged in in vivo-JETPEI® suppressed lung metastasis established by systemic administration of PSPC1-expressing Mahlavu cells according to the schedule in FIG. 7b. PSPC1-CT131 treatment reduced lung metastasis (FIG. 7c), metastatic tumor size (FIG. 7d) and the number of tumor nodules (FIG. 7e). PSPC1-CT131 treatment prolonged survival of mice compared to the group without PSPC1-CT131 treatment (FIG. 7f). IHC analysis of metastatic lung tumor nodules indicated that expression of PSPC1, PTK6 and β-catenin were significantly reduced in PSPC1-CT131-treated mice compared to untreated mice (FIG. 7g). These results suggest that PSPC1-CT131 803 interacts with PSPC1 801 and PTK6 in the nucleus 805 to suppress synergistic oncogenic PSPC1/PTK6 signaling, abolishing autocrine Wnt3a signaling and tumor progression (FIG. 8c).

Phosphorylated-PSPC1 interacts with nuclear PTK6, leading to inhibition of tumor progression (FIG. 8a). PSPC1 801 upregulation or PSPC1-Y523F mutant releases PTK6 nuclear sequestration, synergizing PSPC1 801 and cytoplasmic PTK6 oncogenic effects to modulate Wnt/β-catenin signaling (FIG. 8b). The PSPC1-C-terminal 131 fragment 803, which acts as an inhibitor of oncogenic PSPC1 801 and PTK6, reduces tumor metastasis in HCC.

The cellular determinant switching on oncogenic subcellular translocation of PTK6/β-catenin facilitating tumor cell metastasis remains poorly understood. The invention has revealed PSPC1 as a contextual determinant of subcellular translocations of PTK6/β-catenin and their synergistic tumorigenic signaling. Higher expression of nuclear PTK6 and p-Y523 of PSPC1 in tumors are prognostic biomarkers for HCC patients. PSPC1-CT131, which is an inhibitor targeting oncogenic PSPC1 and PTK6, is a promising clinical intervention for prolonging cancer patient survival. Concordant high expression of nuclear PTK6 and p-Y523 of PSPC1 in lower grades of HCC is associated with a better survival of HCC patients. Higher expression of p-Y523-PSPC1 in early stages of HCC tissues is a favorable prognostic biomarker for HCC patients. Decreased expression of p-Y523-PSPC1 in higher stages of HCC suggests synergistic oncogenic activation of PSPC1, nuclear β-catenin and cytoplasmic PTK6, facilitating HCC tumor progression. PSPC1-CT131 suppressed oncogenic PSPC1- and PTK6/β-catenin-mediated EMT, stemness and tumor progression including autocrine signaling of TGF-β1 and Wnt3a and oncogenic downstream signaling of cytoplasmic PTK6, c-myc and β-catenin. PSPC1-CT131 treatment altered the roles of contextual determinant of subcellular localization switch to sequester the nuclear localization of PTK6, suppress PSPC1-mediated tumor progression and sustain cytoplasmic expression of inactive β-catenin leading to tumor suppression.

Similarly, selinexor (KPT-330), a Selective Inhibitor of Nuclear Export (SINE) targeting CRM1 (chromosome region maintenance 1 protein, exportin 1 or XPO1), has been under clinical trials in divergent cancer types with selective anticancer activity to cancer cells while sparing normal cells. The antineoplastic mechanism of SINE could be due to inhibition of transporting activity of XPO1, resulting in nuclear accumulation of tumor suppressor proteins such as TP53, p27, p21 and others led to tumor suppression. PSPC1-CT131 is a new class of anti-cancer reagent in HCC warranting future examinations of tumor suppressive applications for other types of cancers.

What is claimed is:

1. An isolated plasmid comprising a nucleic acid sequence encoding a C-terminal fragment of paraspeckle component 1 (PSPC1) consisting of the amino acid sequence of SEQ ID NO: 3 that has antitumor activity against tumor cells.

2. The isolated plasmid of claim 1, wherein the tumor cells express PSPC1 and/or protein tyrosine kinase 6 (PTK6).

3. The isolated plasmid of claim 1, wherein the antitumor activity is suppression of tumor cell growth, progression, or metastatasis.

4. A composition comprising: the isolated plasmid of claim 1 and a polymer, polymeric micelle, lipoprotein drug carrier, nanoparticle drug carrier, micelle, liposome, dendrimer, zwitterionic carbon dot, quantum dot, lipid, peptide, polypeptide or protein.

5. The composition of claim 4, wherein the polymer is polyethylenimine (PEI), polypropylenimine (PPI), or a cationic polymer.

6. A method of treating a tumor in a mammal, the method comprising: systemically administering the composition of claim 4 to a mammal that has a tumor that expresses PSPC1 such that the tumor is treated.

7. The method of claim 6, wherein the composition comprises a polymer that is polyethylenimine (PEI), polypropylenimine (PPI), or a cationic polymer.

* * * * *